United States Patent
La et al.

(10) Patent No.: US 11,642,624 B2
(45) Date of Patent: May 9, 2023

(54) METHOD OF REDUCING CARBON DIOXIDE AND AIR POLLUTANTS

(71) Applicant: SK Innovation Co., Ltd., Seoul (KR)

(72) Inventors: Yeon Hwa La, Daejeon (KR); Jae Yang Song, Daejeon (KR); Tae Young Lee, Daejeon (KR); Jae Heum Jung, Daejeon (KR); Tae Wan Kim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 17/579,751

(22) Filed: Jan. 20, 2022

(65) Prior Publication Data

US 2022/0241723 A1    Aug. 4, 2022

(30) Foreign Application Priority Data

Feb. 1, 2021    (KR) .................. 10-2021-0014017

(51) Int. Cl.
*B01D 53/60*    (2006.01)
*C12M 1/00*    (2006.01)

(52) U.S. Cl.
CPC ............ *B01D 53/60* (2013.01); *C12M 21/00* (2013.01); *B01D 2257/302* (2013.01); *B01D 2257/404* (2013.01)

(58) Field of Classification Search
CPC ........ C12R 2001/01; B01D 2258/0283; B01D 2257/504; B01D 2251/95; B01D 53/84; B01D 53/62; B01D 53/50; B01D 2257/302; B01D 2257/404; B01D 53/60; C12M 21/00
See application file for complete search history.

(56) References Cited

U.S. PATENT DOCUMENTS

| | | |
|---|---|---|
| 2013/0189739 A1 | 7/2013 | Jin et al. |
| 2019/0256882 A1 | 8/2019 | Park et al. |
| 2020/0206685 A1 | 7/2020 | La et al. |

FOREIGN PATENT DOCUMENTS

| | | | | |
|---|---|---|---|---|
| CN | 111 249 899 A | * | 6/2020 | ............. B01D 53/48 |
| KR | 1020180034281 A | | 4/2018 | |
| KR | 1020190030159 A | | 3/2019 | |
| WO | 2011056183 A1 | | 5/2011 | |
| WO | WO 2019 234 344 A1 | * | 12/2019 | ................ C12P 7/40 |

* cited by examiner

*Primary Examiner* — Timothy C Vanoy
(74) *Attorney, Agent, or Firm* — The Webb Law Firm

(57) ABSTRACT

The present invention relates to a method of reducing carbon dioxide and air pollutants, and more particularly to a method of simultaneously reducing emissions of carbon dioxide and air pollutants, in which an off-gas containing carbon dioxide, SOx, and NOx is passed through a sulfur-oxidizing microorganism reactor, thereby converting carbon dioxide present in the off-gas into biomass, SOx into sulfate ions, and NOx into amino-N.

2 Claims, No Drawings

METHOD OF REDUCING CARBON DIOXIDE AND AIR POLLUTANTS

CROSS-REFERENCE TO RELATED APPLICATION

This application claims priority to Korean Patent Application No. 10-2021-0014017 filed Feb. 1, 2021, the disclosure of which is hereby incorporated by reference in its entirety.

BACKGROUND OF THE INVENTION

Field of the Invention

The present invention relates to a method of reducing carbon dioxide and air pollutants, and more particularly to a method of simultaneously reducing emissions of carbon dioxide and air pollutants, in which an off-gas containing carbon dioxide, SOx, and NOx is passed through a sulfur-oxidizing microorganism reactor, thereby converting carbon dioxide present in the off-gas into biomass, SOx into sulfate ions, and NOx into amino-N.

Description of Related Art

With increased interest in air pollution due to greenhouse gases, particulate matter and the like worldwide and increasingly stringent regulations on particulate emissions, measures to respond thereto are urgently needed. There are various emission pathways for gases that cause climate change. The main contributor to greenhouse gas emissions is the combustion of fossil fuels, and greenhouse gas emitted through the combustion of fossil fuels accounts for 58% of all gases causing climate change. In combustion plants such as power plants, high-temperature processing gases containing carbon dioxide ($CO_2$), among other components, are generated during the combustion of fuels including coal, oil such as diesel fuel or kerosene fuel, LNG, peat, waste, etc. Due to the increasing need to consider the environment, various processes for removing carbon dioxide from processing gases have been developed, and measures addressing gases causative of climate change are focused on reducing the amount of $CO_2$ gas emitted through combustion of fossil fuels.

With regard to conventional carbon dioxide reduction techniques, Korean Patent Application Publication No. 2018-0034281 discloses a method of converting carbon dioxide into useful materials through a metabolic reaction of a sulfur-oxidizing microorganism. In addition, Korean Patent Application Publication No. 2019-0030159 discloses a method of simultaneously reducing carbon dioxide and metal-containing dust by passing carbon dioxide or an off-gas containing carbon dioxide and metal dust through a sulfur-oxidizing microorganism reactor in which carbon dioxide is used as a carbon source. In addition, International Patent Application Publication No. WO 2011/056183 A1 discloses a biological and chemical process using chemoautotrophic microorganisms for the chemosynthetic fixation of carbon dioxide and/or other inorganic carbon sources into organic compounds.

In addition to carbon dioxide, however, sulfur oxide (SOx) and nitrogen oxide (NOx), among air pollutants, are also components emissions of which are to be reduced. Sulfur oxide is a collective term for oxides of sulfur (S), and mostly includes $SO_2$ (sulfur dioxide) and $SO_3$ (sulfur trioxide). Both are generated when sulfur or fuel containing sulfur is combusted, but in general, $SO_2$ is most abundant, accounting for about 95% of exhaust gas. Sulfur oxide may cause respiratory problems in patients suffering from asthma and children, and it dissolves well in water to form sulfuric acid, which is a major cause of acid rain. Another component, nitrogen oxide (NOx), is generated when nitrogen in the atmosphere reacts with oxygen during combustion of fuel at high temperatures, and is occasionally generated by microorganisms in the soil or water or by lightning. Nitrogen oxide reacts with volatile organic compounds (VOCs) in the atmosphere to form ozone, dissolves in water vapor and thus causes acid rain, and irritates the eyes and respiratory organs.

Therefore, innovative technology capable of solving environmental problems due to greenhouse gases and particulate matter by reducing all of carbon dioxide, sulfur oxide, and nitrogen oxide is required.

Accordingly, the present inventors have made great efforts to solve the above problems, and thus ascertained that, when off-gas containing carbon dioxide and air pollutants is directly passed through a sulfur-oxidizing microorganism incubator, the microorganism uses carbon dioxide in the off-gas as a carbon source, SOx is dissolved in water, oxidized and converted into sulfate ions, and NOx is oxidized by oxygen supplied to the reactor, is dissolved, grows into a source of N for the microorganism and is converted into amino-N, thereby simultaneously reducing emissions of carbon dioxide and air pollutants and effectively solving environmental problems due to greenhouse gases and particulate matter, thus culminating in the present invention.

SUMMARY OF THE INVENTION

It is an object of the present invention to provide a method capable of simultaneously reducing carbon dioxide and air pollutants generated in industrial fields.

In order to accomplish the above object, the present invention provides a method of reducing carbon dioxide and air pollutants including passing an off-gas containing at least one selected from the group consisting of carbon dioxide, SOx, and NOx through a sulfur-oxidizing microorganism reactor.

DESCRIPTION OF THE INVENTION

Unless otherwise defined, all technical and scientific terms used in the present specification have the same meanings as commonly understood by those skilled in the art to which the present disclosure pertains. In general, the nomenclature used in the present specification is well known and commonly used in the art.

In the present invention, it is confirmed that, when an off-gas containing carbon dioxide and air pollutants is directly passed through a sulfur-oxidizing microorganism incubator, the microorganism uses carbon dioxide in the off-gas as a carbon source, SOx is dissolved in water, oxidized, and converted into sulfate ions, and NOx is oxidized by oxygen supplied to the reactor, is dissolved, grows into a source of N for the microorganism, and is converted into amino-N, thereby simultaneously reducing emissions of carbon dioxide and air pollutants and solving environmental problems due to greenhouse gases and particulate matter.

Accordingly, an aspect of the present invention pertains to a method of reducing carbon dioxide and air pollutants including passing an off-gas containing at least one selected from the group consisting of carbon dioxide, SOx, and NOx through a sulfur-oxidizing microorganism reactor.

In the present invention, the off-gas containing at least one selected from the group consisting of carbon dioxide, SOx, and NOx is passed through the sulfur-oxidizing microorganism reactor, so the microorganism uses the carbon dioxide contained in the off-gas as a carbon source, sulfur oxide (SOx) is dissolved in water, oxidized, and converted into sulfate ions, and nitrogen oxide (NOx) is oxidized by oxygen supplied to the reactor, dissolved, used as a nitrogen source for the microorganism, and converted into amino-N.

In the present invention, the sulfur-oxidizing microorganism reactor or a microorganism reactor for producing sulfuric acid is a reactor in which carbon dioxide is selectively used as a carbon source and the sulfur-oxidizing microorganism is cultured in a sulfur-containing medium.

Here, the sulfur-oxidizing microorganism may be a microorganism that grows using reduced sulfur as an energy source and carbon dioxide as a carbon source.

In the present invention, the sulfur-oxidizing microorganism may be at least one selected from the group consisting of bacteria such as *Acidithiobacillus*, *Thiobacillus*, *Thiosphaera*, *Thermothrix*, *Beggiatoa*, *Thioploca*, *Thiodendron*, *Thiobacterium*, *Macromonas*, *Achromatium*, *Thiospira*, *Thioalkalimicrobium*, and *Thioalkalispira*, and archaea such as *Sulfolobus* and *Acidianus*.

In the present invention, more specific examples of the microorganism are as follows.

A. *Acidithiobacillus*: *Acidithiobacillus thiooxidans*, *Acidithiobacillus albertensis*, *Acidithiobacillus caldus*, *Acidithiobacillus cuprithermicus*, *Acidithiobacillus ferridurans*, *Acidithiobacillus ferrivorans*, or *Acidithiobacillus ferrooxidans*

B. *Thiobacillus*: *Thiobacillus denitrificans*

C. *Thiosphaera*: *Thiosphaera pantotropha*

D. *Thermothrix*: *Thermothrix thiopara*

E. *Beggiatoa*: *Beggiatoa alba*, *Beggiatoa leptomitoformis*

F. *Thioploca*: *Thioploca araucae*, *Thioploca chileae*, *Thioploca ingrica*, *Thioploca schmidlei*

G. *Thiodendron*: *Thiodendron latens*

H. *Thiobacterium*: *Thiobacterium bovistum*

I. *Macromonas*: *Macromonas bipunctata*

J. *Achromatium*: *Achromatium oxaliferum*

K. *Thiospira*: *Thiospira winogradskyi*

L. *Thioalkalimicrobium*: *Thioalkalimicrobium aerophilum*, *Thioalkalimicrobium cyclicum*

M. *Thioalkalispira*: *Thioalkalispira microaerophila*

N. *Sulfolobus*: *Sulfolobus solfataricus*

O. *Acidianus*: *Acidianus infernus*

In the present invention, the off-gas may be generated during processing by power plants, petroleum plants, waste combustion plants, or steel mills, and may further include particulate matter in the air.

Hereinafter, preferred examples will be presented to aid in understanding the present invention, but it will be apparent to those skilled in the art that the following examples are merely illustrative of the present invention, and various variations and modifications are possible without departing from the scope and spirit of the present invention. It should be understood that such variations and modifications fall within the scope of the appended claims.

EXAMPLES

Example 1: Pre-Culture of Sulfur-Oxidizing Microorganism 50 ml of a medium containing 1 g/L of $(NH_4)_2SO_4$, 0.5 g/L of $MgSO_4 \cdot 7H_2O$, 250 mg/L of $CaCl_2 \cdot 2H_2O$, 3 g/L of $KH_2PO_4$, 10 mg/L of $FeSO_4 \cdot 7H_2O$, and 10 g/L of sulfur powder was placed in a 100 ml flask, and 1 ml of a sulfur-oxidizing microorganism (*Acidithiobacillus thiooxidans* E29) was inoculated thereto, cultured for 7 days in a shaking incubator at a culture temperature of 30° C. and 150 rpm, and then used for main culture inoculation.

Example 2: Confirmation of SOx and NOx Reduction

Comparative group: 1600 ml of water was placed in a 3 L incubator, after which whether the amounts of SOx and NOx were reduced by water at a temperature of 30° C. and a stirring rate of 800 rpm was evaluated. By recovering the product while supplying fresh water at a dilution rate of 0.5/day, corresponding to the same conditions as a control group, a working volume of 1600 ml was maintained. Here, the supply gas was composed of 95 ccm of mixed gas (30% of $CO_2$, 200 ppm of SOx, 200 ppm of NOx, and the balance of $N_2$) and 890 ccm of air. The amounts of SOx and NOx were analyzed through off-gas analysis once per hour.

Control group: 1600 ml of a medium containing 1 g/L of $(NH_4)_2SO_4$, 0.5 g/L of $MgSO_4 \cdot 7H_2O$, 250 mg/L of $CaCl_2 \cdot 2H_2O$, 3 g/L of $KH_2PO_4$, 10 mg/L of $FeSO_4 \cdot 7H_2O$, and 10 g/L of sulfur powder was placed in a 3 L incubator, after which 50 ml of the pre-culture solution was inoculated thereto, followed by batch culture for 4 days at a pH of 3.5, a temperature of 30° C., and a stirring rate of 800 rpm and then continuous culture recovering the product while a fresh medium having the same composition was added at a dilution rate of 0.5/day. Here, the supply gas was composed of 95 ccm of mixed gas (30% of $CO_2$, 200 ppm of SOx, 200 ppm of NOx, and the balance of $N_2$) and 890 ccm of air. The amounts of SOx and NOx were analyzed through off-gas analysis once or twice per day.

As is apparent from Table 1 below, it was confirmed that 95% or more of SOx was removed in both the comparative group and the control group, and also that NOx was hardly removed in the comparative group but decreased by 45% in the control group. The microorganism concentration in the control group was $4.2 \times 10^7$ cells/ml at the time of initial inoculation, and the microorganism concentration during continuous culture was $8.5 \times 10^9$ cells/ml. It can be found that the microorganism biomass is increased by fixing $CO_2$, which is the sole carbon source.

TABLE 1

| Gas measurement result | SOx (ppm) | NOx (ppm) | SOx removal efficiency [%] | NOx removal efficiency [%] |
| --- | --- | --- | --- | --- |
| Supply gas | 21 | 20 | | |
| Exhaust gas in comparative group | 1.0 | 19 | 95.2 | 5 |
| Exhaust gas in control group | 1.0 | 11 | 95.2 | 45 |

INDUSTRIAL APPLICABILITY

According to the present invention, the method of reducing carbon dioxide and air pollutants is effective at simultaneously reducing emissions of carbon dioxide and air pollutants based on the principle by which CO2 contained in an off-gas is used as a carbon source and NOx subjected to oxidative dissolution is used as an N nutrient source.

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

The invention claimed is:

1. A method of reducing carbon dioxide, $SO_x$ and $NO_x$ simultaneously comprising passing an off-gas containing at least one selected from the group consisting of carbon dioxide, SOx, and NOx through a sulfur-oxidizing microorganism reactor, wherein a sulfur-oxidizing microorganism is a microorganism that grows using reduced sulfur as an energy source and carbon dioxide as a carbon source, and is at least one selected from the group consisting of *Acidithiobacillus, Thiosphaera, Thermothrix, Beggiatoa, Thioploca, Thiodendron, Thiobacterium, Macromonas, Achromatium, Thiospira, Thioalkalimicrobium, Thioalkalispira, Sulfolobus* and *Acidianus*.

2. The method of reducing carbon dioxide, $SO_x$ and $NO_x$ simultaneously of claim 1, wherein the off-gas is generated during a process in a power plant or a steel mill.

* * * * *